United States Patent
Reitz et al.

(10) Patent No.: US 6,441,049 B2
(45) Date of Patent: *Aug. 27, 2002

(54) METHOD OF TREATING NEURODEGENERATIVE DISORDERS VIA INHIBITION OF AMYLOID BETA PEPTIDE BINDING

(75) Inventors: Allen B. Reitz, Lansdale, PA (US); David A. Demeter, Fishers, IN (US); Daniel H. S. Lee, Northhampton; Hoau-Yan Wang, Philadelphia, both of PA (US); Robert H. Chen, Belle Mead, NJ (US); Tina Morgan Ross, Audubon, PA (US); Malcolm K. Scott, Lansdale, PA (US); Carlos R. Plata-Salaman, Ambler, PA (US)

(73) Assignee: Ortho-McNeil Pharmaceutical, Inc., Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,885
(22) Filed: May 27, 1999

Related U.S. Application Data

(60) Provisional application No. 60/087,577, filed on Jun. 1, 1998.

(51) Int. Cl.⁷ ...................... A61K 31/135; C07C 211/00
(52) U.S. Cl. ........................ 514/657; 564/428; 564/429
(58) Field of Search ................................ 564/428, 429; 514/657

(56) References Cited

U.S. PATENT DOCUMENTS

| | | | |
|---|---|---|---|
| 4,988,700 A | 1/1991 | Traber et al. | 514/255 |
| 5,554,601 A | 9/1996 | Simpkins et al. | 514/182 |

FOREIGN PATENT DOCUMENTS

| | | |
|---|---|---|
| CH | 637 363 | 7/1983 |
| EP | 360 077 | 3/1990 |

OTHER PUBLICATIONS

Kihara et al., "Nicotinic receptor stimulation protects neurons against beta–amyloid toxicity", Annals of Neurology, Aug. 1997, vol. 42, No. 2, 159–163.
Kihara et al., Neuroprotective effect of nicotine–related substances against beta–amyloid cytotoxicity, Neurosci. Res., 1997, p. S158, abstract 1230.
Itoh et al., "Dysfuction of Cholinergic and dopaminergic neuronal systems in beta–amyloid protein–infused rats" J. Neurochem, vol. 66, 1996, pp. 1113–1117.
Salomon et al., "Nicotine inhibits amyloid formation by the beta–peptide", Biochemistry, vol. 35 No. 42, 1996, pp. 13568–13578.
Maurice et al., "Amnesia induced in mice by centrally administered beta–amyloid peptides involves cholinergic dysfuction" Brain Res., vol. 706, No. 2, 1996 pp. 181–193.
Auld et al., "Beta–amyloid peptides as direct cholinergic neuromodulators: a missing link?"Trends Neurosci, vol. 21, No. 1, Jan. 1998 pp. 43–49.
Zamani et al., "Nicotine modulates the neurotoxic effect of beta–amyloid protein (25–35) in hippocampal cultures" Neuroreport vol. 8, No. 2, Jan. 1997, pp. 513–517.
Sjoberg et al., "Neuronal nicotinic receptor activaion : a promising strategy for the treatment of Alzheier's disease?" Int. J. Geriatric Psychopharacology, vol. 1, No. 3, 1998, pp. 145–149.
McDermed et al., "Synthesis and pharmacology of some 2–aminotetralins Dopamine receptor Agonists", J. Med. Chem., vol. 18, No. 4, 1975, pp. 362–367.
Auld et al., Trends Neurosci, (1998) 21, 43–49.
Arneric et al., Arch Int Pharmacodyn, (1982) 258, 84–89.
Seiler and Markstein, Mol Pharmacol, (1984) 26, 452–457.
Atwal et al., J Med Chem, (1987) 30, 627–635.
Mellin et al., J Med Chem, (1988) 31, 1130–1140.

*Primary Examiner*—Deborah C. Lambkin
(74) *Attorney, Agent, or Firm*—Mary A. Appollina

(57) ABSTRACT

The invention is directed to a method of treating a neurodegenerative disorder in a subject in need thereof which comprises administering to the subject an amount of a compound effective to inhibit the interaction of amyloid-beta with alpha-7 nicotinic acetylcholine receptors.

14 Claims, No Drawings

METHOD OF TREATING NEURODEGENERATIVE DISORDERS VIA INHIBITION OF AMYLOID BETA PEPTIDE BINDING

CROSS-REFERENCE TO RELATED APPLICATION

This application claims priority from U.S. provisional application Ser. No. 60/087,577, filed Jun. 1, 1998, the contents of which are hereby incorporated by reference.

FIELD OF THE INVENTION

The present invention provides a method for treating neurodegenerative disorders. More particularly, a method for treating neurodegenerative disorders (e.g., Alzheimer's disease) by inhibiting the interaction of amyloid beta with alpha-7 nicotinic acetylcholine receptors.

BACKGROUND OF THE INVENTION

Neurodegenerative disorders such as Alzheimer's disease (AD) and Parkinson's disease (PD) afflict humanity with great suffering and financial loss. AD is characterized by neurofibrillary tangles, neuritic plaques, and neuronal cell death. AD appears as either the familial, early onset (<60 yrs) or late-onset (>60 yrs) forms, with the latter being more prevalent. AD is the major cause of age-related dementia and cognitive impairment (Wisniewski, T.; Ghiso, J.; Frangione, B. *Neurobiol. of Disease* 1997, 4, 313–328). The amyloid precursor protein (APP), β-amyloid$_{1-40}$ (Aβ$_{1-40}$), and β-amyloid$_{1-42}$ (Aβ$_{1-42}$) are keenly involved in the pathology of AD. The Aβ peptides are derived from APP by proteolytic processing. Dramatic evidence implicating the Aβ peptides, particularly Aβ$_{1-42}$, in AD comes from various recently identified mutations accounting for certain types of inherited AD. Such mutations in the presenilin (PS1 and PS2) genes are probably the cause of the most frequent form of familial, early-onset AD (Rogaev, E. I. *Molecular Biology* 1998, 32, 58). In these cases, as with APP mutations, more Aβ$_{1-42}$ is observed relative to Aβ$_{1-40}$. Extensive studies have shown that Aβ$_{1-42}$ has a greater ability than Aβ$_{1-40}$ to aggregate into the amyloid fibrils that constitute the plaques characteristic of AD (Lansbury, P. T., Jr. *Accts. Chem. Res.* 1996, 29, 317). Even though Aβ$_{1-40}$ is generally present to a much larger degree in the cerebrospinal fluid than Aβ$_{1-42}$, it is Aβ$_{1-42}$ which is the major Aβ peptide found in AD plaques.

The Aβ peptides can inhibit cholinergic neurotransmitter function independent of neurotoxicity (Auld, D. S.; Kar, S.; Quirion, R. *Trends Neurosci.* 1998, 21, 43). Aβ peptides bind to a number of natural substances such as apoE3, apoE4, apoJ, transthyretin, and albumin. In addition, Aβ has been reported to interact with a membrane-bound receptor for advanced glycation end products and to the class A scavenger receptor (SR) associated with the production of reactive oxygen species. Stimulation of the alpha-7 subtype of the nicotinic acetylcholine receptors (nAChRs) can protect neurons against Aβ cytotoxicity (Kihara, T. et al. *Ann. Neurol.* 1997, 42, 159). Also, a set of compounds that activate nAChRs, especially of the alpha-7 subtype, have been found to have in vivo activity in models of cognition enhancement (U.S. Pat. No. 5,741,802, issued Apr. 21, 1998).

We now describe specific binding of Aβ$_{1-40}$ and Aβ$_{1-42}$ to the alpha-7 subtype of nAChRs. This new finding has broad ramifications for the etiology and treatment of AD. nAChRs are members of the ligand-gated ion channel family and appear to be formed from five protein subunits associating together around a central pore (Lindstrom, *J. Molecular Neurobiology* 1997, 15, 193). These subunits include α1-α9, β1-β4, γ, δ, and ε. The α7 subtype forms functional homomers which bind to α-bungarotoxin, a 75-amino acid peptide, with high affinity (0.65–1.7 nM K$_d$) and nicotine with relatively low affinity (ca. micromolar K$_d$) (Holladay, M. W.; Dart, M. J.; Lynch, J. K. *J. Med. Chem.* 1997, 40, 4169).

Compounds which block the aggregation of Aβ peptides are potentially useful drugs for the treatment of AD. For example, rifampicin inhibits Aβ aggregation and neurotoxicity and may show an effect in vivo in diminishing plaque burden when compared with age-matched controls (Tomiyama, T. et al. *J. Biol. Chem.* 1996, 271, 6839). In order to block the interaction of the Aβ peptides with α7 nAChRs, compounds can be found to either bind to α7 nAChRs, to Aβ itself, or to both. Any of these mechanisms of action would be expected to provide significant protection against Aβ-mediated neurotoxicity and inhibition of cholinergic functioning mediated by nAChRs and be extremely useful for the treatment of AD. The binding of Aβ$_{1-42}$ to alpha-7 nAChRs provides a seed for crystallization or deposition of Aβ into insoluble deposits, which have the potential to grow into the fibrillar amyloid deposits characteristic of AD. Therefore, blocking the interaction of Aβ$_{1-42}$ with alpha-7 nAChRs should reduce the amount of insoluble aggregated Aβ that is formed, and thus prevent the neurotoxicity and pathology associated with such aggregated amyloid deposits.

Accordingly, it is an object of the invention to provide a method for treating neurodegenerative disorders by inhibiting the binding of amyloid beta peptides to alpha-7 nicotinic acetylcholine receptors. It is a further object of the invention to provide a method for treating Alzheimer's disease and/or for slowing the progression of Alzheimer's disease by inhibiting the binding of amyloid beta peptides to alpha-7 nicotinic acetylcholine receptors. Another object of the invention is to provide a predictive method, a method for diagnosis, a method to monitor prognosis, a method to monitor the progression, and a method to monitor the therapeutic efficacy for any therapeutic intervention used in Alzheimer's disease. Still another object of the invention is to provide a method for identifying compounds which inhibit the binding of Aβ peptides with α7 nAChRs, either by binding to Aβ peptides or to α7 nAChRs.

SUMMARY OF THE INVENTION

The present invention is directed to a method of treating a neurodegenerative disorder in a subject (preferably, a human) in need thereof which comprises administering to the subject an amount of a compound effective to inhibit the binding of an amyloid beta peptide, preferably Aβ$_{1-42}$, to alpha-7 nAChRs, preferably, human alpha-7 nAChRs. Since alpha-8 and alpha-9 nAChRs are similar with respect to structure and function to alpha-7 nAChRs, it is possible that blocking the interaction of β-amyloid with alpha-8 and alpha-9 nAChRs would have therapeutic benefit as well.

Neurodegenerative disorders included within the methods of the present invention include, but are not limited to, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Sträussler-Scheinker disease, Kuru and fatal familial insomnia).

Other conditions also included within the methods of the present invention include age-related dementia and other dementias and conditions with memory loss including vascular dementia, diffuse white matter disease (Binswanger's disease), dementia of endocrine or metabolic origin, dementia of head trauma and diffuse brain damage, dementia pugilistica and frontal lobe dementia. Also other neurodegenerative disorders resulting from cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

Preferably, the neurodegenerative disorder is selected from Alzheimer's disease, Parkinson's disease, Tourette's syndrome, amyotrophic lateral sclerosis, age-related memory loss, senility and age-related dementia, most preferably, the neurodegenerative disorder is Alzheimer's disease. Because, most preferably, the neurodegenerative disorder is Alzheimer's disease, also defined as an amyloidosis, other conditions within the methods of the present invention include other amyloidosis which share features including, but not limited to, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

In one embodiment of the invention is a method of treating and/or preventing dementia in an Alzheimer's patient (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities) which comprises administering to the subject a therapeutically effective amount of a compound to inhibit the binding of an amyloid beta peptide (preferably, $A\beta_{1-42}$) with nAChRs, preferable alpha-7 nAChRs, most preferably, human alpha-7 nAChRs.

In a second embodiment of the invention is a method of improving memory and/or mental status and/or of halting the progression of mental deterioration in an Alzheimer's disease patient which comprises administering to the subject a therapeutically effective amount of a compound to inhibit the binding of an amyloid beta peptide (preferably, $A\beta_{-1-42}$) with nAChRs, preferably alpha-7 nAChRs, most preferably, human alpha-7 nAChRs.

Preferably, the compound used in the methods of treating neurodegenerative disorders, treating and/or preventing Alzheimer's disease, and improving memory and/or halting the progression of mental deterioration in an Alzheimer's disease patient is not estrogen, raloxifene, droloxifene, tamoxifen, idoxifene or levomeloxifene; more preferably, the compound is not estrogen or a selective estrogen receptor modulator (SERM). A SERM is an estrogen receptor ligand that exhibits estrogen agonist activity in the cardiovascular system, CNS and bone, and estrogen antagonist activity in reproductive tissues, such as breast and uterus.

Also included in the invention is the use of a compound which inhibits the binding of an amyloid beta peptide (preferably $A\beta_{1-42}$) to an alpha-7 nAChR (preferably, a human alpha-7 nAChR) in the preparation of a medicament for the treatment of a neurodegenerative disorder in a subject (preferably, a human) in need thereof.

Another illustration of the invention is the use of a compound which inhibits the binding of an amyloid beta peptide (preferably $A\beta_{1-42}$) to alpha-7 nAChRs (preferably, human alpha-7 nAChRs) in the preparation of a medicament for: a) improving memory, b) halting the progression of the mental deterioration seen in Alzheimer's disease patients, c) treating dementia, d) preventing dementia in an Alzheimer's patient, and e) treating and/or preventing other clinical manifestations of Alzheimer's disease that include, but are not limited to, cognitive and language deficits, apraxias, depression, delusions and other neuropsychiatric symptoms and signs, and movement and gait abnormalities in an Alzheimer's patient.

In another aspect of the invention is a compound of the formula I:

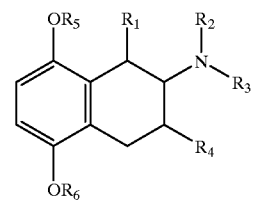

wherein $R_1$ is hydrogen or $C_1$–$C_4$ alkyl;

$R_2$ is selected from hydrogen, $C_1$–$C_6$ alkyl, aryl or $C_7$–$C_{10}$ aralkyl;

$R_3$ is selected from hydrogen, $C_1$–$C_6$ alkyl, $C_3$–$C_{10}$ alkenyl, $C_3$–$C_8$ cycloalkyl$C_1$–$C_6$ alkyl, $C_1$–$C_6$ alkoxycarbonyl$C_1$–$C_6$ alkyl, $C_1$–$C_6$ alkylthio, heteroaryl$C_1$–$C_4$ alkyl, unsubstituted or substituted aryl or unsubstituted or substituted $C_7$–$C_{10}$ aralkyl wherein the substituent on the aryl or aralkyl are one or more substituents independently selected from the group consisting of halogen, hydroxy, $C_1$–$C_6$ alkyl and unsubstituted or substituted $C_1$–$C_6$ alkoxy wherein the substituents on the alkoxy are one or more substituents independently selected from amino, $C_1$–$C_6$ alkylamino, $C_1$–$C_6$ dialkylamino, pyrrolidinyl, piperidinyl, azepinyl or morpholinyl; or $R_2$ and $R_3$, together with the nitrogen to which they are attached, form a five or six-membered heterocyclic ring selected from pyrrolidinyl, piperidinyl, morpholinyl, thiomorpholinyl or piperazinyl;

$R_4$ is $C_1$–$C_6$ alkyl, aryl, or $C_7$–$C_{10}$ aralkyl; and $R_5$ and $R_6$ are each independently selected from hydrogen, $C_1$–$C_6$ alkyl, $C_3$–$C_{10}$ alkenyl, $C_1$–$C_8$ alkylcarbonyl, or diphenylphosphinyl; and pharmaceutically acceptable salts and prodrugs thereof.

In preferred compounds of formula I, $R_1$ is hydrogen;

$R_2$ is selected from hydrogen or $C_1$–$C_4$ alkyl;

$R_3$ is selected from $C_1$–$C_4$ alkyl, $C_3$–$C_{10}$ alkenyl, $C_5$–$C_6$ cycloalkyl$C_1$–$C_{4_6}$ alkyl, $C_1$–$C_6$ alkoxycarbonyl$C_1$–$C_4$ alkyl, $C_1$–$C_6$ alkylthio, heteroaryl$C_1$–$C_4$ alkyl, or unsubstituted or substituted $C_7$–$C_{10}$ aralkyl wherein the substituent on the aralkyl are one or two substituents independently selected from the group consisting of halogen, hydroxy, $C_1$–$C_4$ alkyl and unsubstituted or substituted $C_1$–$C_4$ alkoxy wherein the substituents on the alkoxy are one or two substituents independently selected from amino, $C_1$–$C_4$ alkylamino, $C_1$–$C_4$ dialkylamino, pyrrolidinyl, or piperidinyl; or $R_2$ and $R_3$, together with the nitrogen to which they are attached, form a morpholinyl ring;

$R_4$ is $C_1$–$C_4$ alkyl; and $R_5$ and $R_6$ are each independently selected from hydrogen, $C_1$–$C_4$ alkyl, $C_3$–$C_6$ alkenyl, $C_1$–$C_6$ alkylcarbonyl, or diphenylphosphinyl.

In a subclass of compounds of formula I are compounds having the formula

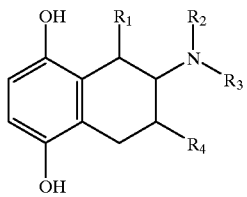

wherein $R_1$ is hydrogen or $C_1$–$C_4$ alkyl;

$R_2$ and $R_3$ are each independently selected from hydrogen, $C_1$–$C_6$ alkyl, aryl or $C_7$–$C_{10}$ aralkyl; and $R_4$ is $C_1$–$C_6$ alkyl, aryl, or $C_7$–$C_{10}$ aralkyl;

and pharmaceutically acceptable salts thereof.

Compounds of formula I are novel compounds which block the interaction of beta-amyloid with alpha-7 nAChRs. More specifically, the compounds of formula I inhibit the binding of $A\beta_{1-42}$ with human alpha-7 nAChRs by binding to $A\beta_{1-42}$. The orientation between the nitrogen atom and $R_4$ on the appropriate ring can be either cis or trans. Preferably, the compound is 5,8-dihydroxy-trans-2-di(N-propylamino)-3-methyl-1,2,3,4-tetrahydronaphthalene, and pharmaceutically acceptable salts thereof.

Other compounds useful in the methods of the present invention inhibit the binding of $A\beta_{1-42}$ with human alpha-7 nAChRs by binding to human alpha-7 nAChRs directly. An example of such a compound which binds to human alpha-7 nAChRs is α-bungarotoxin.

DETAILED DESCRIPTION OF THE INVENTION

The present invention provides methods of treating neurodegenerative disorders by inhibiting the binding of amyloid beta peptides to alpha-7 nAChRs. Neurodegenerative disorders included within the methods of the present invention include, but are not limited to, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Sträussler-Scheinker disease, Kuru and fatal familial insomnia).

Other conditions also included within the methods of the present invention include age-related dementia and other dementias and conditions with memory loss including vascular dementia, diffuse white matter disease (Binswanger's disease), dementia of endocrine or metabolic origin, dementia of head trauma and diffuse brain damage, dementia pugilistica and frontal lobe dementia. Also other neurodegenerative disorders resulting from cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

Preferably, the neurodegenerative disorder is selected from Alzheimer's disease, Parkinson's disease, Tourette's syndrome, amyotrophic lateral sclerosis, age-related memory loss, senility and age-related dementia, most preferably, the neurodegenerative disorder is Alzheimer's disease. Because, most preferably, the neurodegenerative disorder is Alzheimer's disease, also defined as an amyloidosis, other conditions within the methods of the present invention include other amyloidosis which share features including, but not limited to, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

The terms "amyloid beta", "amyloid beta peptide" or "beta-amyloid" as used herein, refer to amyloid beta peptides and include the $A\beta_{1-40}$, $A\beta_{1-42}$ and $A\beta_{1-43}$ peptides and their fragments. Examples of fragments of amyloid beta peptides that have been shown to have biological activity and are useful in the methods of the present invention include, but not limited to, fragment 1-28, and fragment 25-35 (e.g., Yatin S M, Aksenov M, Butterfield D A. Neurochem Res 1999 Mar;24(3):427–35; Hirakura Y, Satoh Y, Hirashima N, Suzuki T, Kagan B L, Kirino Y. Biochem Mol Biol Int 1998 Nov; 46(4):787–94; Mazziotti M, Perlmutter D H. Biochem J 1998 Jun 1;332 (Pt 2):517–24; Perovic S, Bohm M, Meesters E, Meinhardt A, Pergande G, Muller W E. Mech Ageing Dev 1998 Mar 16;101 (1–2):1–19; Muller W E, Eckert G P, Scheuer K, Cairns N J, Maras A, Gattaz W F. Amyloid 1998 Mar;5(1):10–5; Butterfield D A, Martin L, Carney J M, Hensley K. Life Sci 1996;58(3):217–28; Forloni G, Lucca E, Angeretti N, Della Torre P, Salmona M. J Neurochem 1997 Nov;69(5):2048–54; Heese K, Hock C, Otten U. J Neurochem 1998 Feb;70(2):699–707; Blanchard B J, Konopka G, Russell M, Ingram V M. Brain Res 1997 Nov 21;776(1–2):40–50; Wu A, Derrico C A, Hatem L, Colvin R A. Neuroscience 1997

Oct;80(3):675–84; Muller W E, Romero F J, Perovic S, Pergande G, Pialoglou P. J Neurochem 1997 Jun;68(6):2371–7; Suh Y H. J Neurochem 1997 May;68(5):1781–91; Parpura-Gill A, Beitz D, Uemura E. Brain Res 1997 Apr 18;754(1–2):65–71; Fletcher T G, Keire D A. Protein Sci 1997 Mar;6(3):666–75; Scorziello A, Meucci O, Calvani M, Schettini G. Neurochem Res 1997 Mar;22(3):257–65); Miguel-Hidalgo J J, Vecino B, Fernandez-Novoa L, Alvarez A, Cacabelos R. Eur Neuropsychopharmacol 1998 Aug;8(3):203–8; Maneiro E, Lombardi V R, Lagares R, Cacabelos R. Methods Find Exp Clin Pharmacol 1997 Jan–Feb; 19(1):5–12).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "alkyl" shall mean straight or branched chain alkanes of one to ten carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 2 to 10 carbon atoms, or any number within this range.

The term "aryl" indicates aromatic groups such as phenyl and naphthyl.

The term "$C_7$–$C_{10}$ aralkyl" means an alkyl group substituted with an aryl group wherein the total number of carbon atoms is between 7 and 10 (e.g., benzyl, phenylethyl, phenylpropyl).

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom that results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl. Prefered heteroaryl groups include pyridyl, pyrrolyl, pyrazinyl, thiadiazolyl, pyrazolyl, thienyl, triazolyl and quinolinyl.

The term "$N(CH_2)_5$" means a piperidinyl group.

The term "$cC_6H_{11}$" refers to a cyclohexyl group.

When a particular group is "substituted" (e.g., aryl, aralkyl), that group may have one or more substituents, preferably from one to five substituents, more preferably from one to three substituents, most preferably from one to two substituents, independently selected from the list of substituents.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula

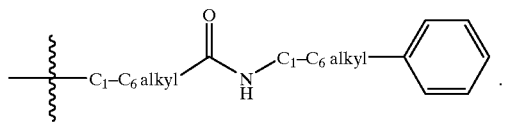

Compounds which are useful in the methods of the present invention for inhibiting the interaction of $A\beta_{1-40}$ and $A\beta_{1-42}$ to the alpha-7 subtype of nAChRs for either the purpose of direct therapeutic intervention or in order to screen for compounds which act via this mechanism include compounds of formula I, especially 5,8-dihydroxy-trans-2-di(N-propylamino)-3-methyl-1,2,3,4-tetrahydronaphthalene (Compound 9), (−)-nicotine, (rac)-epibatidine, α-bungarotoxin, and pharmaceutically acceptable salts thereof.

Certain peptide stretches of the human alpha-7 nAChR bind to amyloid beta and can be used in place of the alpha-7 nAChR together with amyloid beta for the purpose of screening libraries to find compounds which block the interaction of amyloid beta and the human alpha-7 nAChR. Included among these peptide stretches of the human alpha-7 nAChR are alpha-7 nAChR193-224 and smaller peptides derived thereof as listed in the Table.

TABLE

| Compound | Amelioration of the $A\beta_{1-42}$ Meditated Inhibition of ACh Release in Rat Cortical Synaptosomes (%) |
|---|---|
| human alpha-7 nAChR193–224 Ac-NGEWDLVGIPGKRSERFYECCKEPYPDVTFTV-NH2 | 81% at 10 μM 79% at 1 μM |
| human alpha-7 nAChR200–214 Ac-GIPGKRSERFYECCK-NH2 | 79% at 10 μM 71% at 1 μM |
| human alpha-7 nAChR206–216 Ac-SERFYECCKEP-NH2 | 81% at 10 μM 77% at 1 μM |
| human alpha-7 nAChR206–216 oxidized (cyclic) CC: Ac-SERFYECCKEP-NH2 | 84% at 10 μM 82% at 1 μM |
| human alpha-7 nAChR206–216 SERFYECCKEP | 22% at 10 μM 10% at 1 μM |
| human alpha-7 nAChR210–213 Ac-YECC-NH2 | 72% at 10 μM 59% at 1 μM |

The standard one-letter code for the amino acids has been employed for the compounds. This code is listed in Lehninger, A. I. "Biochemistry" Second Edition, Worth Publishers, Inc., New York, 1976, p 73–75.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds of this invention include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope prodrugs of the compounds of this invention. A prodrug is inactive as administered, but becomes activated in vivo. The prodrug is converted to the parent drug chemically or by specific enzyme(s). Higuchi, T.; Stella, V., Eds. "Pro-Drugs as Novel Drug Delivery Systems"; American Chemical Society: Washington, D.C., 1976. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

(−)-Nicotine is (−)-1-methyl-2-(3-pyridinyl)pyrrolidine and is readily available from Sigma Chemical Company.

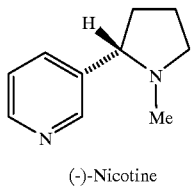

(-)-Nicotine (+/−)-Epibatidine is exo-(+/−)-2-(6-chloro-3-pyridinyl)-7-azabicyclo[2.2.1]heptane and is readily available from Sigma Chemical Company.

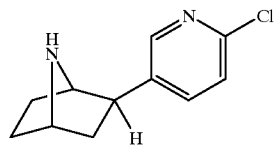

(rac)-Epibatidine

α-Bungarotoxin is a 74 amino acid peptide which is commercially available from Research Biochemicals Inc. α-Bungarotoxin and its amino acid sequence are described in Lee, C. Y. *Annu. Rev. Pharmacol.* 1972, 12, 265– 281.

$^{125}$I-Aβ$_{1-40}$, fluo-Aβ$_{1-40}$, and anti-alpha-7 nAChR antibodies are commercially available Amersham Pharmacia Biotech, Advanced Bioconcepts and Research Biochemicals International, respectively.

$^{125}$I-α-bungarotoxin is commercially available from Amersham Pharmacia Biotech.

The present invention therefore provides a method of treating a neurodegenerative disorder, which comprises administering any of the compounds as defined herein in a quantity effective to treat the neurodegenerative disorder. Preferably, the compound is not estrogen, raloxifene, droloxifene, tamoxifen, idoxifene or levomeloxifene; more preferably, the compound is not estrogen or a selective estrogen receptor modulator (SERM). The compound may be administered to a patient afflicted with a neurodegenerative disorder by any conventional route of administration, including, but not limited to, intravenous, oral, subcutaneous, intramuscular, intradermal, buccal, intracerebral and other parenteral routes. The quantity of the compound which is effective for treating a neurodegenerative disorder is between 0.01 mg per kg and 10 mg per kg of subject body weight.

The method of treating neurodegenerative disorders described in the present invention may also be carried out using a pharmaceutical composition comprising any of the compounds as defined herein and a pharmaceutically acceptable carrier. The pharmaceutical composition may contain between about 0.5 mg and 200 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, capsules, granules, tablets, caplets, and powders, and liquid forms, such as solutions, syrups, elixers, and suspensions. Forms useful for intracerebral and other parenteral routes of administration include sterile solutions, emulsions and suspensions.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, body weight, diet, physical activity and time of administration, and associated co-morbidities and clinical conditions will result in the need to adjust dosages.

The present invention also provides diagnostic tools useful for diagnosing Alzheimer's disease. Alzheimer's disease (AD) exhibits neuropathological abnormalities in the olfactory system located in the nasal cavity. These include the presence of dystrophic neurites that exhibit immunoreactivity for tau, neurofilaments, apolipoprotein E and other proteins, abnormal tau protein, increase in superoxide dismutase, and beta-amyloid deposition in the primary sensory (olfactory receptor) cells and nerve fibres of the nasal mucosa tissue (Arnold et al., Ann N Y Acad Sci 1998 Nov 30;855:762–75; Hock et al., Eur Neurol 1998 Jul;40(1):31–6; Johnson et al., Neurobiol Aging 1994 Nov–Dec; 15(6):675–80; Kulkarni-Narla et al., Exp Neurol 1996 Aug;140(2):115–25; Lee et al., Exp Neurol 1993 May;121(1):93–105; Tabaton et al., Neurology 1991 Mar;41 (3):391–4; Talamo et al., Ann N Y Acad Sci 1991;640:1–7; Yamagishi et al., Ann Otol Rhinol Laryngol 1998 May;107(5 Pt 1):421–6; Yamagishi et al., Nippon Jibiinkoka Gakkai Kaiho 1994 Jan;97(1):51–60). These observations recapitulate the neuropathological profile and neurodegenerative abnormalities (e.g., cytoskeletal changes, protein immunoreactivity and beta-amyloid deposition) observed in central nervous system neurons from AD patients. Routine access to these sensory neurons and fibers can be done with nasal biopsy in AD patients (e.g., Feron et al., Arch Otolaryngol Head Neck Surg 1998 Aug;124(8):861–6).

Olfactory neuroblasts (olfactory neurons obtained by biopsy and placed in primary cell culture) from AD patients produce carboxy terminal amyloid precursor protein (APP) fragments that contain beta-amyloid (A-beta)(Crino et al., Ann Otol Rhinol Laryngol 1995 Aug;104(8):655–61). Crino et al. showed labeling of A-beta in the basal third of the olfactory neuroepithelium and in axons projecting through the lamina propria of AD patients. Thioflavin-S staining that detects amyloid deposition was also observed in the basal third of the olfactory neuroepithelium from AD patients. Alpha 7 nicotinic acetylcholine receptors are present in olfactory neurons probably including olfactory receptor cells in the nasal cavity (Alkondon et al., Neurosci Lett 1994 Aug 1;176(2):152–6; Alkondon et al., Eur J Neurosci 1997 Dec;9(12):2734–42; Bouvet et al., Neurosci Res 1988 Feb;5 (3):214–23; Edwards et al., Experientia 1987 Aug 15;43(8):868–73; Edwards et al., Experientia 1988 Mar 15;44(3):208–11; Seguela et al., J Neurosci 1993 Feb;13(2):596–604).

Beta-amyloid peptide increases cytosolic-free $Ca^{2+}$ in AD lymphoblasts (Ibarreta et al., Alzheimer Dis Assoc Disord 1997 Dec;11(4):220–7), and elevates mitogen-induced $Ca^{2+}$ responses in freshly prepared human lymphocytes (Eckert et al., Life Sci 1994;55(25–26):2019–29). Amyloid precursor protein (APP) can be induced on the cell surface of human lymphocytes upon stimulation (Bullido et al., Biochim Biophys Acta 1996 Aug 21;1313(1):54–62) and increased APP-770 isoform occurs in lymphocytes from AD patients (Ebstein et al., Brain Res Mol Brain Res 1996 Jan;35(1–2):260–8). Lymphoblastoid cells from patients with early-onset and late-onset familial AD show increased expression of beta-APP mRNA and protein (Matsumoto et al., Eur J Biochem 1993 Oct 1;217(1):21–7). Lymphocytes from AD patients also exhibit an increased mRNA level for alpha 7 nicotinic receptor (Hellstrom-Lindahl et al., Brain Res Mol Brain Res 1999 Mar 20;66(1–2):94–103)

Based on the information described above, we propose that the analysis of the alpha 7 nicotinic acetylcholine receptor—beta amyloid peptides interaction in circulating blood cells and olfactory neuroepithelial neurons/neuronal processes or olfactory neuroblasts obtained from AD patients could be used as AD diagnostic tools, markers of AD progression and prognosis, and markers of therapeutic efficacy for any intervention or treatment targeting AD.

Thus, the present invention provides methods for diagnosing Alzheimer's disease, monitoring the progression and prognosis of Alzheimer's disease and/or monitoring the therapeutic efficacy of any intervention or treatment of Alzheimer's disease comprising:

(a) obtaining a test sample from a subject wherein the test sample comprises circulating blood cells and/or olfactory neuroepithelial neuronal cell bodies or their neuronal processes (i.e., dendrites and axon of a nueron); and (b) analyzing the test sample for interaction of an amyloid beta peptide (including, but not limited to, $A\beta_{1-40}$, $A\beta_{1-42}$ and $A\beta_{1-43}$ peptides and their fragments) with alpha-7 nicotinic acetylcholine receptors.

The compounds of formula I, such as 5,8-Dihydroxy-trans-2-di(N-propylamino)-3-methyl-1,2,3,4-tetrahydronaphthalene (Compound 9), are made according to the procedures described in the Schemes and Examples which follow.

Abbreviations used in the instant specification, particularly the Schemes and Examples, are as follows:

Ac=acetyl
Ach=acetylcholine
AcOH=acetic acid
BSA=bovine serum albumin
DMF=N,N-dimethyl formamide
DMSO=dimethyl sulfoxide
$Et_3N$=triethyl amine
EtOAc=ethyl acetate
FCS=fetal calf serum
i-Pr=isopropyl
Me=methyl
MeI=methyl iodide
nAChR=nicotinic acetylcholine receptor
Ph=phenyl
PCC=pyridinium chlorochromate
TEA=triethyl amine
THF=tetrahydrofuran
TLC=thin layer chromatography

SCHEME 1

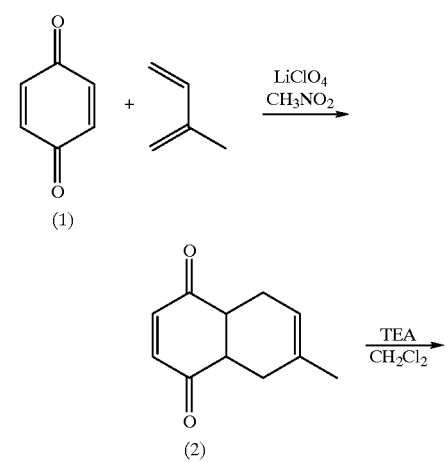

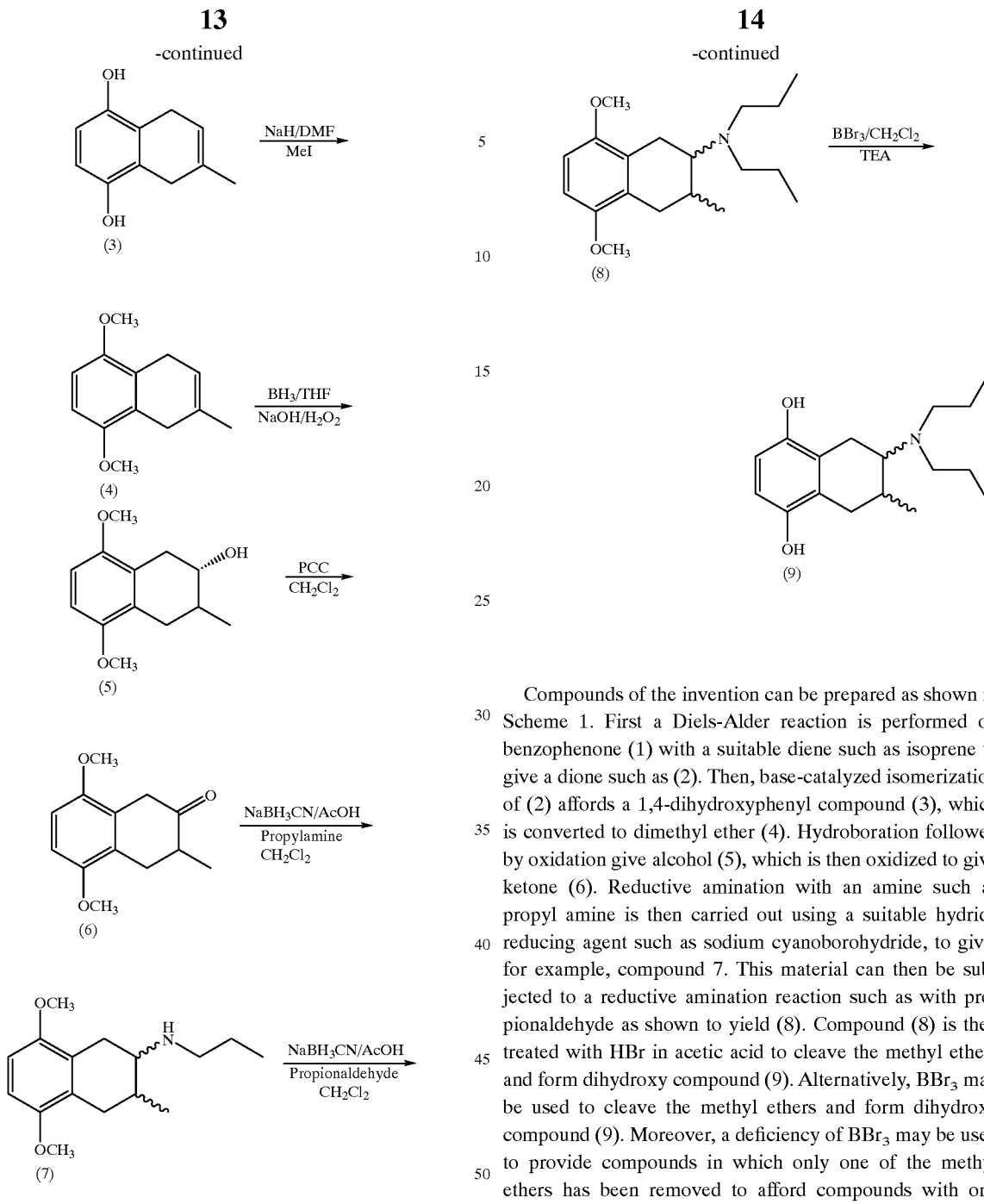

Compounds of the invention can be prepared as shown in Scheme 1. First a Diels-Alder reaction is performed on benzophenone (1) with a suitable diene such as isoprene to give a dione such as (2). Then, base-catalyzed isomerization of (2) affords a 1,4-dihydroxyphenyl compound (3), which is converted to dimethyl ether (4). Hydroboration followed by oxidation give alcohol (5), which is then oxidized to give ketone (6). Reductive amination with an amine such as propyl amine is then carried out using a suitable hydride reducing agent such as sodium cyanoborohydride, to give, for example, compound 7. This material can then be subjected to a reductive amination reaction such as with propionaldehyde as shown to yield (8). Compound (8) is then treated with HBr in acetic acid to cleave the methyl ethers and form dihydroxy compound (9). Alternatively, BBr₃ may be used to cleave the methyl ethers and form dihydroxy compound (9). Moreover, a deficiency of BBr₃ may be used to provide compounds in which only one of the methyl ethers has been removed to afford compounds with one hydroxy and one methoxy group.

Scheme 2

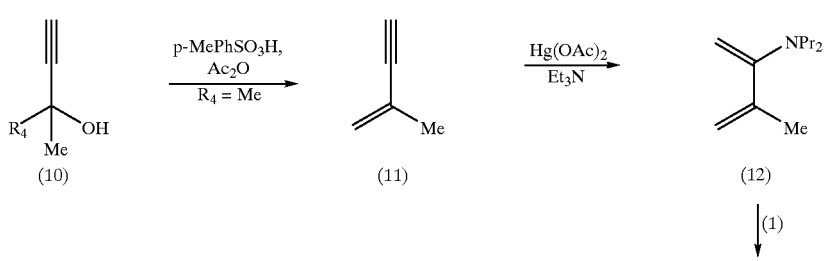

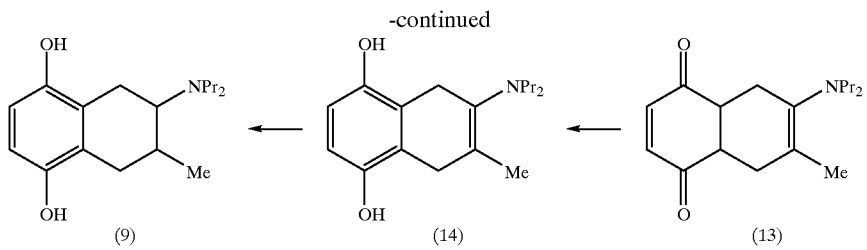

A further means of preparing compounds of the present invention is illustrated in Scheme 2. A suitable propargyl alcohol, such as 3-hydroxy-3-methyl-1-butyne (10, $R_4$=Me) is dehydrated to give an enyne such as compound 11. This material is then subjected to an aminomercuration reaction to afford a 2-amino-1,4-butadiene such as compound (12). Diels-Alder reaction of compound (12) with benzophenone (1) gives (13) which can be isomerized as in Scheme 1 with base to give the 1,5-dihyroxy compound (14). Reduction of the double bond of (14) catalytically with hydrogen and palladium on carbon, such as 10% palladium on carbon, yields compounds of the invention such as (15).

Compounds of type 9 can be treated with a base such as triethylamine in a suitable solvent such as dioxane or methylene chloride along with electrophiles such as acid halides, phosphinyl halides, or alkyl halides to give the products of substitution on one or both of the phenolic hydroxyls. Such compounds can be active by themselves, or serve as prodrugs for compound 9.

The following Examples are set forth to aid in the understanding of the invention, and are not intended and should not be construed to limit in any way the invention set forth in the claims which follow thereafter.

EXAMPLE 1

Preparation of 5,8-Dihydroxy-trans-2-di(N-propylamino)-3-methyl-1,2,3,4-tetrahydronaphthalene (9)

a. 5,8-Dihydroxy-2-methyl-1,4-dihydronaphthalene (3)

To a solution of p-benzoquinone (10.00 g, 92.5 mmol) in 1M solution of lithium perchlorate, in nitromethane (300 mL) was added isoprene (9.24 mL, 92.3 mmol) at room temperature. The resultant reaction mixture was stirred at room temperature under $N_2$ for 4 hours. The reaction mixture was partitioned between EtOAc (500 mL) and water (200 mL). The organic layer was washed with brine, dried over sodium sulfate and concentrated to give 2 as brown solid. The reaction was repeated on 15 g of benzoquinone to afford additional 2. These two runs were combined and carried on without further purification. To a solution of 2 (35.00 g, 199 mmol) in methylene chloride (400 mL) was added triethylamine (40 mL). The reaction mixture was stirred at room temperature for 1 hr. The product was precipitated out of solution by the addition of hexane (300 mL). The solid was collected by filtration and dried in a dessicator under high vaccuum overnight to provide 3 as a light brown solid.

$^1$H NMR (300 MHz, DMSO-$d_6$): δ 1.75 (s, 3H), 3.00–3.01 (m, 2H), 3.09 (s, 2H), 5.53 (s, 1 H), 6.43 (s, 2H), 8.49–8.52 (m, 2H).

b. 5,8-Dimethoxy-2-methyl-1,4-dihydronaphthalene (4)

To a cold (–78° C.) solution of hydroquinone 3 (17.00 g, 96.6 mmol) in DMF under $N_2$ was added unwashed 60% sodium hydride in mineral oil (8.90 g, 222.5 mmol). The resultant reaction mixture was warmed to room temperature over a 30 min period and subsequently treated with methyl iodide (14.3 mL, 230 mmol). After stirring the reaction mixture for 1 hr at room temperature the reaction mixture was diluted with ethyl acetate (1.5 L) and washed with brine (3×500 ml). The organic solution was dried over sodium sulfate, filtered, concentrated, and the residue purified on silica gel (elution with 20% ethyl acetate\hexane) to afford 4 as a light yellow oil which solidified upon standing.

$^1$H NMR (300 MHz, $CD_3OD$): δ 1.77 (s, $CH_3$), 3.07–3.09 (m, 2H), 3.16 (br s, 2H), 3.73(s, 3H), 3.75 (s, 3H), 5.52–5.53 (m, 1H), 6.65 (s, 2H).

c. 5,8-Dimethoxy-trans-2-hydroxy-3-methyl-1,2,3,4-tetrahydronaphthalene (5)

A solution of 4 (5.00 g, 24.5 mmol) in tetrahydrofuran (100 ml) was cooled to 0° C. and treated with 1 M borane-tetrahydrofuran complex (24.5 mL, 24.5 mmol) and the resulting solution was stirred at room temperature for 4 h. Then, 12 mL of 3 N NaOH solution was added slowly to the stirring reaction solution followed by the addition of 6 mL of 30% aqueous hydrogen peroxide. After stirring for 30 min, the resultant mixture was diluted with 500 mL of ethyl acetate and washed by brine (2×100 mL). The organic layer was dried over sodium sulfate, filtered and concentrated, and the residue was purified on silica gel (30% ethyl acetate\hexane) to give 5 as a white solid.

$^1$H NMR (300 MHz, $CDCl_3$): δ 1.13 (d, 3H, J=6.51 Hz), 1.60 (d, 1H), 1.75–1.90 (m, 1H), 2.26 (dd, 1H, J=10.0 Hz, 17.57 Hz), 2.48 (dd, 1H, J=8.93 Hz, 17.10 Hz), 2.96 (dd, 1H, J=5.31, 17.7 Hz), 3.16 (dd, 1H, J=5.33, 5.35 Hz), 3.63–3.69 (m, 1H), 3.78 (s, 6H), 6.62 (s, 2H).

d. 5,8-Dimethoxy-3-methyl-2-tetralone (6)

A solution of alcohol 5 (10 g, 45 mmol) and dichloromethane (200 mL) at –30° C. was treated dropwise with oxalyl chloride (4.92 g, 24 mL, 0.275 mol). The reaction was stirred at –30° C. for 30 min, cooled to –60° C., and DMSO (6.4 mL) was added slowly over 15 min. The reaction was stirred for one hour, cooled to –78° C. for 30 min, and then treated dropwise with triethylamine (40 mL). The reaction was warmed to room temperature and stirred for 1 hr, followed by the addition of water and dichloromethane with thorough mixing. The organic layer was separated, dried with $MgSO_4$, filtered and the solvent was evaporated to an oil. Purification of this material using flash chromatography (flash silica, 70/30: hexane/EtOAc) afforded 6 as a white crystalline solid.

$^1$H NMR (300 MHz, $CDCl_3$) δ 6.7 (q, 2 H), 3.78 (s, 3 H), 3.75 (s, 3 H), 3.5 (dd, 2 H), 3.3 (m, 1 H), 2.55 (m, 2 H), 1.2 (d, 3 H).

e. 5,8-Dimethoxy-2-N-propylamino-3-methyl-1,2,3,4-tetrahydronaphthalene (7)

To a solution of 6 (0.15 g, 0.68 mmol) in acetonitrile (10 mL) was added sodium cyanoborohydride (0.085 g, 1.30 mmol), 0.05 ml of acetic acid and N-propylamine (0.08 mL, 1.3 mmol). The resulting solution was stirred at room temperature overnight and poured into 10 mL of 1 N NaOH solution. The mixture was extracted with EtOAc, dried over sodium sulfate, concentrated, and the residue purified by preparative TLC (elution with 30% ethyl acetate in hexane) to give amine 7 as a colorless oil.

$^1$H NMR (300 MHz, CD$_3$OD): δ 0.85 (d, 3H, J=7.07 Hz), 0.93–0.97 (m, 3H), 1.09 (t, 2H), 1.49–1.61 (m, 2H), 2.12–2.42 (m, 2H), 2.51–2.76 (m, 4H), 2.82–3.08 (m, 2H), 3.73 (s, 3H), 3.74 (s, 3H), 6.65 (s, 2H).

f. 5,8-Dimethoxy-trans-2-di(N-propylamino)-3-methyl-1,2,3,4-tetrahydronaphthalene (8)

To a solution of 7 (0.11 g 0.42 mmol) in acetonitrile (10 ml) was added sodium cyanoborohydride (0.05 gm, 0.6 mmol), 0.03 mL of acetic acid and propionaldehyde (0.045 mL, 0.60 mmol). The resulting solution was stirred at room temperature overnight and poured into 10 mL of 1N NaOH solution. The mixture was extracted with EtOAc, dried over sodium sulfate, concentrated, and the residue was purified by preparative TLC (elution with 30% ethyl acetate in hexane) to give amine 8 as a light yellow solid.

$^1$H NMR (300 MHz, CD$_3$OD): δ 0.84 (d, 3H, J=6.94 Hz), 0.92 (t, 2H, J=7.30, 7.32 Hz), 1.27–1.59 (m, 4H), 2.33–2.42 (m, 2H), 2.54–3.02 (m, 8H), 3.73 (s, 3H), 3.76 (s, 3H), 6.66 (s, 2H).

In a similar manner was prepared compounds 19, 21, 25, 27, 29, 35, 37, 39, 41, 52, and 54.

In order to separate the enantiomers of 8, 2.859 g of 8 was passed through a CHIRALPAK® AD™ chiral cellulose-based high pressure liquid chromatography column (8 cm×30 cm) at 25° C. using hexane/isopropyl alcohol (99/1) as the eluant to give two fractions as oils. Fraction 1 (18) had a 98.6% enantiomeric excess (e.e.) and fraction 2 (17) had a 97.9% e.e. Fraction 1 (0.306 g, 1.0 mmol) and fumaric acid (0.141 g, 1.2 mmol) were dissolved in ethanol (2 mL) with heating. The ethanol was evaporated and the residue triturated with diethyl ether affording the fumarate salt of 18 as a white solid. Similarly obtained from Fraction 2 (0.301 g, 1.0 mmol) and fumaric acid (0.141 g, 1.2 mmol) was the fumarate sale of 17.

g. 5,8-Dihydroxy-trans-2-di(N-propylamino)-3-methyl-1,2,3,4-tetrahydronaphthalene (9)

A mixture of 8 (1.4 g, 4.6 mmol) and 3.5 mL of 48% aqueous HBr in acetic acid (3.5 mL) was stirred at 100° C. under N$_2$ overnight. The reaction mixture was then cooled to 0° C. and extracted with diethyl ether (20 mL). The organic solution was neutralized with aqueous NaHCO$_3$ and separated. The aqueous layer was extracted with ether (20 mL) and the combined ether solutions were dried over Na$_2$SO$_4$, filtered, and concentrated to give 9.

$^1$H NMR (600 MHz, CDCl$_3$): δ 0.86–0.92 (dt, 6H), 1.13 (d, 3H, J=6.42 Hz), 1.42–1.50 (m, 4H), 1.88–1.93 (m, 1H), 2.23–2.28 (m, 1H), 2.39–2.52 (m, 6H), 2.61–2.63 (m, 1H), 2.90 (dd, 1H, J=4.75, 16.28 Hz), 2.95 (dd, 1H, J=5.05, 16.75 Hz), 4.84 (br s, 2 H), 6.50 (dd, 2H, J=8.52 Hz). CI-MS: m/e MH$^+$278 (40%).

In a similar manner 17 and 18 were converted to 15 and 16 respectively. Additionally, demethylation of the appropriate dimethyl ethers by the procedure described here led to the preparation of compounds 20, 22, 26, 28, 30, 32, 34, 36, 40, 42, 53, and 55. In the course of the demethylation of 37, the butyl ether was also removed to obtain 38.

EXAMPLE 2

Preparation of 5,8-Dihydroxy-cis-2-(1-morpholinyl)-3-methyl-1,2,3,4-tetrahydronaphthalene (24)

a. 5,8-Dimethoxy-cis-2-(1-morpholinyl)-3-methyl-1,2,3,4-tetrahydronaphthalene (23).

Ketone 6 (0.299 g, 1.36 mmol) was dissolved in toluene (1 mL) followed by the addition of morpholine (0.130 g, 0.13 mL, 1.5 mmol) and Ti(i-PrO)$_4$ (0.611 g, 0.64 mL, 2.15 mmol). The reaction mixture was stirred for 15 hrs at room temperature. Methanol (2 mL) was added followed by portionwise addition of NaBH$_4$ (0.15 g, 3.9 mmol) over 1 hr. Dichloromethane and 1N NaOH were added with thorough mixing and the organic layer was separated, dried with MgSO$_4$, filtered and evaporated to an oil. Purification of this material using flash chromatography (flash silica, 75/25:hexane/EtOAc) afforded product 23.

$^1$H NMR (300 MHz, DMSO-d$_6$) δ 6.6 (s, 2 H), 3.6 (d, 6 H), 3.5 (s, 4 H), 3.2 (s, 4 H), 3.2 (s, 6 H), 2.8 (d, 1 H), 2.7 (d, 1 H), 2.3 (m, 2 H), 2.05 (m, 2 H), 0.6 (d, 3 H).

b. 5,8-Dihydroxy-cis-2-(1-morpholinyl)-3-methyl-1,2,3,4-tetrahydronaphthalene (24).

A solution of 23 (20 mg, 0.066 mmol) and dichloromethane (2 mL) at −78° C. was treated with a 1 M solution of BBr$_3$ in dichloromethane (1 mL, 1 mmol.) and stirred for 1 hr at −78° C. After warming to room temperature, methanol (5 mL) was added and the solvents were evaporated. Methanol addition to the residue followed by evaporation was done twice. The residue was dissolved in acetonitrile (25 mL) and treated with triethylamine (2 mL). After stirring for 2 hrs, water and ethyl acetate were added with thorough mixing. The organic layer was separated, dried with MgSO$_4$, filtered, and solvent evaporated to yield 24 as an oil.

$^1$H NMR (300 MHz, CD$_3$OD) δ 6.7 (s, 2 H), 3.4 (m, 4 H), 3.3 (m, 1 H), 2.6 (m, 5 H), 1.9 (m, 1 H), 1.5 (m, 2 H), 1.05 (d, 3 H), 0.9 (m, 3 H).

EXAMPLE 3

Preparation of 5,8-Dimethoxy-cis and trans-2-(N-propyl-N-propargyl)amino-3-methyl-1,2,3,4-tetrahydronaphthalene (31 and 33)

Ketone 6 (1 g, 4.5 mmol) was dissolved in acetonitrile (75 mL) followed by the addition of acetic acid (0.54 mL, 9 mmol, 2 eq.) and propargylamine (0.6 mL, 9 mmol, 2 eq.). The reaction mixture was stirred at room temperature for 1 hr. Sodium cyanoborohydride (0.6 g, 9 mmol, 2 eq.) was added portionwise (3x) over 1.5 hrs (every 30 min), and the reaction mixture was stirred overnight at room temperature. Ethyl acetate and 1 N NaOH were added with thorough mixing and the organic layer was separated, dried with MgSO$_4$, filtered and evaporated to an oil. The product was purified with flash chromatography (50:50/ethyl acetate:hexane) to yield an oil of 5,8-dimethoxy-cis and trans-2-N-(propargyl)amino-3-methyl-1,2,3,4-tetrahydronaphthalene (1.2 g, 100%). This material was dissolved in acetonitrile along with propionaldehyde (0.65 g, 9 mmol, 2 eq.) and acetic acid (0.5 mL, 9 mmol) and stirring for 1 hr at room temperature. One hour later, sodium cyanoborohydride (0.6 g, 9 mmol, 2 eq.) was added portionwise (3x) over 1.5 hours (every 30 mins). The reaction was stirred overnight at room temperature. Ethyl acetate and 1 N NaOH were added to the reaction with thorough mixing and the organic layer was separated, dried with MgSO$_4$, filtered and evaporated to a mixture of products 31 and 33. Purification of this material using flash chromatography (flash silica, 80:20/hexane:ether) afforded product 31 and 33. Compound $^1$H NMR (300 MHz, CDCl$_3$) δ 6.6 (s, 2 H), 3.8 (s, 6 H), 3,4 (q, 2 H), 3.0 (dd, 2 H), 2.6 (m, 4 H), 2.2 (m, 2 H), 1.85 (m, 1 H), 1.5 (m, 2 H), 1.1 (d, 3 H), 0.9 (t, 3 H).

Compound 33: $^1$H NMR (300 MHz, CDCl$_3$) δ 6.6 (s, 2 H), 3.78 (s, 3 H), 3.75 (s, 3 H), 3.6 (q, 2 H), 3.05 (dd, 1 H), 2.75 (m, 2 H), 2.61 (m, 3 H), 2.3 (m, 2 H), 2.1 (s,1 H), 1.55 (m, 2 H), 0.9 (t, 3 H), 0.8 (d, 3 H).

EXAMPLE 4

Preparation of 5-[2-(3-Methyl)butenyl]-8-hydroxy-trans-2-di(N-propylamino)-3-methyl-1,2,3,4-tetrahydronaphthalene (43); and 5-Hydroxy-8-[2-(3-methyl)butenyl]-trans-2-di(N-propylamino)-3-methyl-1,2,3,4-tetrahydronaphthalene (44)

Diol 9 (0.3 g, 1.2 mmol) was dissolved in acetone (40 mL) followed by the addition of potassium carbonate (0.19 g) and 1-bromo-3-methyl-2-butene (0.1 mL, 0.87 mmol). The reaction mixture was stirred for 48 hrs at room temperature. Dichloromethane and water were added with thorough mixing and the organic layer was separated, dried with $MgSO_4$, filtered and the solvent was evaporated to yield an oil. Purification of this material using flash chromatography (flash silica, 70:30/hexane:ether) afforded products 43 and 44. The regiochemical structural assignment between the two of them is uncertain. Compound 43: $^1$H NMR (300 MHz, $CDCl_3$) δ 6.5 (s, 2 H), 5.5 (t, 1 H), 4.4 (m, 2 H), 3.0 (m, 2 H), 2.4 (m, 8 H), 1.8 (m, 1 H), 1.72 (s, 3 H), 1.65 (s, 3 H), 1.4 (m, 4 H), 1.1 (dd, 3 H), 0.85 (t, 6 H). Compound 44: $^1$H NMR (300 MHz, $CDCl_3$) δ 6.55 (s, 2 H), 5.45 (t, 1 H), 4.4 (m, 2 H), 3.05 (dd, 1 H), 2.85 (dd, 1 H), 2.4 (m, 7 H), 1.65 (s, 3 H), 1.6 (s, 3 H), 1.55 (m, 2 H), 1.4 (m, 4 H), 1.1 (m, 4 H), 1.1 (d, 3 H), 0.9 (t, 6 H).

EXAMPLE 5

Preparation of 5-Hydroxy-8-methoxy-trans-2-di(N-propylamino)-3-methyl-1,2,3,4-tetrahydronaphthalene (45); and 5-Methoxy-8-hydroxy-trans-2-di(N-propylamino)-3-methyl-1,2,3,4-tetrahydronaphthalene (46)

Compound 8 (1.85 g, 6 mmol) was dissolved in dichloromethane (20 mL) and cooled to −78° C., followed by the addition of boron tribromide (6 mL of a 1 M solution, 6 mmol, 1 eq.). The reaction mixture was stirred at −78° C. for 1 hr and then warmed to room temperature for 2 hrs. The reaction was quenched with methanol (5 mL), and the solvent was evaporated (methanol quench repeated twice more). The resulting oil was dried overnight under high vacuum (5 mm Hg). The residue was dissolved in dichloromethane and $NaHCO_3$ was added, mixed thoroughly, and the organic layer was separated, dried with $MgSO_4$, filtered and the solvent evaporated to a mixture of two regioisomers 45 and 46 (1:1). The purification of a mixture (200 mg) was conducted on a reverse phase HPLC (C18 column, 69:30:1/water:acetonitrile:triflouroacetic acid) to afford 45 and 46 as triflouroacetate salts. Compound 45 (TFA salt): $^1$H NMR (300 MHz, $CDCl_3$) δ 6.65 (q, 2H), 4.7 (bs, 1 H), 3.7 (s, 3 H), 3.5 (m, 1 H), 3.3 (m, 1 H), 3.0 (m, 4H), 2.7 (m, 2 H), 2.3 (m, 1 H), 2.0 (m, 5 H), 1.15 (d, 3 H), 0.9 (m, 6 H). Compound 46 (free base): $^1$H NMR (300 MHz, $CDCl_3$) δ 6.55 (q, 2 H), 4.3 (bs, 1 H), 3.75 (s, 3 H), 3.05 (dd, 1 H), 3.0 (dd, 1 H), 2.6 (m, 1 H), 2.4 (m, 6 H), 2.2 (m, 1 H), 1.8 (m, 1 H), 1.4 (m, 4 H), 1.1 (d, 3 H), 0.85 (t, 6 H). The regiochemistry of the structure of 46 was confirmed through careful analysis of HMBC (Heteronuclear Multiple Bond Correlation) connectivities and nOe effects. The structure of 46 was established by connectivity between the methoxy substituent on the aromatic ring and the benzylic methylene adjacent to the methyl-substituted carbon.

EXAMPLE 6

Preparation of 5,8-Dimethoxy-2-[N-(L-alanyl methyl ester)]-3-methyl-1,2,3,4-tetrahydronaphthalene (48)

Ketone 6 (1 g, 4.5 mmol) was dissolved in acetonitrile (75 mL) and acetic acid (0.54 mL, 9 mmol, 2 eq.), and alanine methyl ester hydrochloride (1.3 g, 9 mmol, 2 eq.) was added. The reaction was stirred at room temperature for 1 hr, and then sodium cyanoborohydride (0.6 g, 9 mmol, 2 eq.) was added portionwise (3×) over 1.5 hrs (every 30 min). The reaction was stirred overnight at room temperature. Ethyl acetate and 1 N NaOH were added with thorough mixing and the organic layer was separated, dried with $MgSO_4$, filtered and evaporated to an oil. The product was purified with flash chromatography (50:50/ethyl acetate:hexane) to yield 48 as an oil. Compound 48, (mixture of cis and trans stereoisomers) $^1$H NMR (300 MHz, $CDCl_3$) δ 6.64 (d, 2 h), 4.2 (m, 1 H), 3.85 (m, 3 H, 3.75 (s, 6 H), 3.5 (m, 1 H), 3.1 (m, 2 H), 2.8 (m, 2H), 2.55 (m, 1 H), 2.3 (m, 1 H), 1.7 (m, 3 H), 1.2 (m, 3 H).

EXAMPLE 7

Preparation of 5,8-Dimethoxy-2-[N-(L-alanyl methyl ester)-N-propyl]-3-methyl-1,2,3,4-tetrahydronaphthalene (47)

Compound 48 (0.28 g, 0.8 mmol) was dissolved in acetonitrile along with propionaldehyde (0.1 mL, 1.6 mmol, 2 eq.) and acetic acid (0.2 mL, 1.6 mmol), and stirred for 1 hr at room temperature. One hour later, sodium cyanoborohydride (0.2 g, 1.6 mmol, 2 eq.) was added portionwise (3×) over a period of 1.5 hrs (every 30 minutes). The reaction was stirred overnight at room temperature. Ethyl acetate and 1 N NaOH were added to the reaction with thorough mixing and the organic layer was separated, dried with $MgSO_4$, filtered and evaporated to an oil. This material was purified using flash chromatography (flash silica, 80:20/hexane:ether) to afford (1:1 mixture of cis and trans stereoisomers) 47. $^1$H NMR (300 MHz, $CDCl_3$) δ 6.6 (d, 2 H), 3.75 (s, 6 H), 3.7 (d, 4 H), 3.0 (m, 2 H), 2.65 (m, 3 H), 2.2 (m, 1 H), 1.7 (m, 2 H), 1.45 (m, 2 H), 1.25 (d, 3 H), 1.0 (m, 3 H), 0.8 (t, 3 H).

EXAMPLE 8

Preparation of 5-Diphenylphosphinoyl-8-hydroxy-trans-2-di(N-propylamino)-3-methyl-1,2,3,4-tetrahydronaphthalene (58); and 5,8-bis (Diphenylphosphinoyl)-3-methyl-1,2,3,4-tetrahydronaphthalene (59)

Compound 9 (0.5 g, 2.0 mmol) was dissolved in dioxane (100 mL) at 0° C. Triethylamine (6 mL) was added and the reaction mixture was stirred at 0° C. for 30 mins, followed by the addition of diphenylphosphinyl chloride (0.84 mL, 4.4 mmol). The reaction mixture was stirred overnight at room temperature. $NaHCO_3$ and dichloromethane were then added with thorough mixing. The organic layer was separated, dried with $MgSO_4$, filtered and the solvent was evaporated to a crude oil which was purified by flash chromatography (flash silica, 70:30/hexane:ether) to yield 59 and 58. Compound 59: $^1$H NMR (300 MHz, $CDCl_3$) δ 7.85 (d, 4 H), 7.8 (d, 4 H), 7.5 (m, 12 H), 6.8 (q, 2 H), 3.0 (m, 2 H), 2.4 (m, 7 H), 1.8 (m, 1 H), 1.4 (m, 4 H), 1.05 (d, 3 H), 0.85 (t, 6 H). Compound 58 (1:1 mix of regioisomers): $^1$H NMR (300 MHz, $CDCl_3$) δ 7.85 (m, 4 H), 7.5 (m, 6 H), 6.6 (q, 1 H), 6.48 (s, 1 H), 6.21 (d, 1 H), 2.9 (m, 3 H), 2.3 (m, 9 H), 1.65 (m, 1 H), 1.4 (m, 1 H), 1.05 (d, 3 H), 0.85 (m, 6 H). In a similar manner, starting from 32, was prepared both compounds 57 and 56. In addition, in a similar manner, starting from 9, was prepared compounds 49–51 using the appropriate reagents.

EXAMPLE 9

Preparation of 5,8-Dimethoxy-cis-2-[N-(4-(2-(1-piperidinyl)ethoxy)phenyl)]amino-3-methyl-1,2,3,4-tetrahydronaphthalene (60)

A solution of 1-(2-chloroethoxy)-4-nitrobenzene (2.01 g, 0.01 mol), piperidine (2.55 g, 0.03 mol), and toluene (10 mL) was refluxed overnight. The reaction mixture was filtered and the filtrate evaporated to give 2.97 g of 1-[2-(1-piperidinyl)ethoxy]4-nitrobenzene as an orange oil, MS M+ (m/e) 251.18. This material (1.25 g, 0.004 mol) was hydrogenated in ethanol (25 mL) in the presence of 10% Pd—C catalyst at 40 psig and 25° C. overnight. Filtration and evaporation of the reaction mixture gave 0.95 g of 4-[2-(1-piperidinyl)ethoxy]aniline as a light brown oil, MS M+ (m/e) 221.24. A solution of this oil (0.220 g, 1.0 mmol), 3-methyl-5,8-dimethoxy-2-tetralone (6, 0.206, 0.94 mmol), and 1,2-dichloroethane (3.5 mL) was treated with sodium triacetoxyborohydride (0.300 g, 1.4 mmol) and acetic acid (0.060 g, 1.0 mmol) and the resulting mixture was stirred overnight at 25° C. The reaction was treated with 3N sodium hydroxide solution with vigorous stirring. The organic layer was separated, washed with saturated sodium chloride solution, dried over potassium carbonate, filtered and evaporated to a red oil. This material was purified by C-18 reverse phase high pressure liquid chromatography affording compound 60 as a pink solid. $^1$H NMR (300 MHz, CDCl$_3$): δ 7.10–7.22 (m, 2H), 6.52–6.82 (m, 4H), 4.25–4.33 (m, 2H), 3.60–3.80 (m, 3H), 3.75 (s, 3H), 3.71 (s, 3H), 3.48–3.38 (m, 2H), 2.80–3.05 (m, 4H), 1.80–2.10 (m, 4H), 1.10–1.50 (m, 3H), 1.00 (d, 3H). MS M+ (m/e) 425.38.

The compounds shown in Table 1, below, were prepared according to the procedures described herein.

TABLE 1

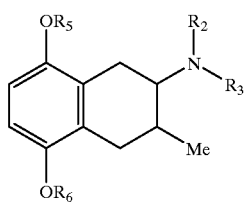

| Cp. | R$_5$ | R$_6$ | R$_2$ | R$_3$ | Config. | MS M+ (m/e) |
|---|---|---|---|---|---|---|
| 9 | H | H | Pr | Pr | trans | 278.24 |
| 15 | H | H | Pr | Pr | trans, ent. | 278.25 |
| 16 | H | H | Pr | Pr | trans, ent. | 278.21 |
| 7 | Me | Me | H | Pr | trans | |
| 8 | Me | Me | Pr | Pr | trans | 306.28 |
| 17 | Me | Me | Pr | Pr | trans, ent. | 306.24 |
| 18 | Me | Me | Pr | Pr | trans, ent. | 306.27 |
| 19 | Me | Me | Pr | Ph(CH$_2$)$_3$ | trans | 382.28 |
| 20 | H | H | Pr | Ph(CH$_2$)$_3$ | trans | 354.27 |
| 21 | Me | Me | Pr | cC$_6$H$_{11}$CH$_2$ | trans | 360.32 |
| 22 | H | H | Pr | cC$_6$H$_{11}$CH$_2$ | trans | 332.32 |
| 23 | Me | Me | —(CH$_2$)$_2$O(CH$_2$)$_2$— | | cis | 292.66 |
| 24 | H | H | —(CH$_2$)$_2$O(CH$_2$)$_2$— | | cis | 264.28 |
| 25 | Me | Me | Pr | CH$_2$Ph | trans | 354.74 |
| 26 | H | H | Pr | CH$_2$Ph | trans | 326.21 |
| 27 | Me | Me | Pr | MeS(CH$_2$)$_3$ | trans | 352.29 |
| 28 | H | H | Pr | MeS(CH$_2$)$_3$ | trans | 324.24 |
| 29 | Me | Me | Pr | (2-thienyl)CH$_2$ | trans | 360.24 |
| 30 | H | H | Pr | (2-thienyl)CH$_2$ | trans | 332.14 |
| 31 | Me | Me | Pr | CH$_2$CCH | trans | 302.21 |
| 32 | H | H | Pr | CH$_2$CCH | trans | 274.16 |
| 33 | Me | Me | Pr | CH$_2$CCH | cis | 302.22 |
| 34 | H | H | Pr | CH$_2$CCH | cis | 274.16 |
| 35 | Me | Me | Pr | CH$_2$(4-IPh) | trans | 480.11 |
| 36 | H | H | Pr | CH$_2$(4-IPh) | trans | 452.14 |
| 37 | Me | Me | Pr | CH$_2$(4-BuOPh) | trans | 426.25 |
| 38 | H | H | Pr | CH$_2$(4-OHPh) | trans | 342.16 |
| 39 | Me | Me | Pr | CH$_2$(2-ClPh) | trans | 388.18 |
| 40 | H | H | Pr | CH$_2$(2-ClPh) | trans | 360.12 |
| 41 | Me | Me | Pr | CH$_2$(4-MePh) | trans | 368.29 |
| 42 | H | H | Pr | CH$_2$(4-MePh) | trans | 340.18 |
| 43 | H | X | Pr | Pr | trans | 346.29 |

TABLE 1-continued

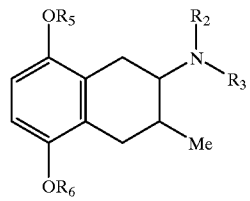

| Cp. | R$_5$ | R$_6$ | R$_2$ | R$_3$ | Config. | MS M+ (m/e) |
|---|---|---|---|---|---|---|
| 44 | X | H | Pr | Pr | trans | 346.30 |
| 45 | Me | H | Pr | Pr | trans | 292.22 |
| 46 | H | Me | Pr | Pr | trans | 292.22 |
| 47 | Me | Me | Pr | CH(Me)CO$_2$Me | cis & trans | 350.26 |
| 48 | Me | Me | H | CH(Me)CO$_2$Me | cis & trans | 308.19 |
| 49 | Y | Y | Pr | Pr | trans | 446.39 |
| 50 | H | Y | Pr | Pr | trans | 362.26 |
| 51 | Y | H | Pr | Pr | trans | 362.30 |
| 52 | Me | Me | Pr | Me | trans | 278.19 |
| 53 | H | H | Pr | Me | trans | 250.18 |
| 54 | Me | Me | Pr | Z | trans | 402.28 |
| 55 | H | H | Pr | Z | trans | 374.25 |
| 56 | H | X' | Pr | CH$_2$CCH | trans | 474.13 |
| 57 | X' | X' | Pr | CH$_2$CCH | trans | 674.11 |
| 58 | H | X' | Pr | Pr | trans | 478.21 |
| 59 | X' | X' | Pr | Pr | trans | 678.11 |
| 60 | Me | Me | H | Y' | cis | 425.38 |

X = —CH$_2$CH=CMe$_2$
Y = —C(O)-t-Bu
Z = —CH$_2$CH$_2$CH(Me)CH$_2$CH$_2$CH=CMe$_2$
X' = P(O)Ph$_2$
Y' = 4-[(2-(1-piperidinyl)ethyl)oxy]Ph

EXAMPLE 10

As a specific embodiment of an oral composition, 100 mg of Compound 9 from Example 1 is formulated with sufficient finely divided lactose to provide a total amount of 580 to 590 mg to fill a size O hard gel capsule.

EXAMPLE 11

Aβ$_{1-42}$ and Aβ$_{1-40}$ Binding to Alpha-7 nAChRs can be Demonstrated in Competitive Binding Experiments with α-bungarotoxin SK-N-MC cell membranes were incubated with 0.5 nM of $^{125}$I-α-bungarotoxin in the presence of various concentrations of Aβ$_{1-42}$ and Aβ$_{1-40}$ at 25° C. for 1 hr. The assay mixture was then rapidly filtered and the radioactivity that was retained on the filter was determined. These studies showed that both Aβ$_{1-42}$ and Aβ$_{1-40}$ inhibited $^{125}$I-α-bungarotoxin binding in a concentration-dependent manner with IC$_{50}$ values of 1 pM and 100 pM, respectively.

EXAMPLE 12

Aβ$_{1-42}$ Binding to Alpha-7 nAChRs is Supported by Competitive Binding Experiments with $^{125}$I-Aβ$_{1-40}$ and Provides a Seed for Amyloid Deposition and, thus, Incipient Plaque Formation Alpha-7 nAChRs were immobilized on wheat germ agglutinin coupled yittrium SPA beads and allowed to incubate with $^{125}$I-Aβ$_{1-40}$ in the presence of various concentrations of cold Aβ$_{1-40}$ or Aβ$_{1-42}$. The data showed that 0.1 femtoM of cold Aβ$_{1-42}$ completely abolished the binding, suggesting that Aβ$_{1-42}$ interacted with alpha-7 nAChRs with high affinity. However, in the presence of 10 nM of cold $A\beta_{1-42}$, the total binding of $^{125}I\text{-}A\beta_{1-40}$ to alpha-7 nAChRs was dramatically increased. We attribute this increase of binding at higher concentrations to $A\beta_{1-42}$-induced precipitation of the $A\beta$ peptides on the membranes. Prolonged incubation at lower concentrations also revealed that total binding was increased in reactions even with 100 pM of cold $A\beta_{1-42}$. In control experiments, 80 pM $^{125}I\text{-}A\beta_{1-40}$ did not bind appreciably, along with 1 pM to 1 nM of $A\beta_{1-40}$, to 30 µg of Bowes melanoma membranes. Thus, $A\beta$ deposition can occur on biological cell membranes containing alpha-7 nAChRs, but does not occur non-specifically on control membranes, suggesting that alpha-7 nAChRs can specifically seed the aggregation of β-amyloid in biological systems.

EXAMPLE 13

$A\beta_{1-42}$ Binding to Alpha-7 nAChRs is of Higher Affinity than $A\beta_{1-40}$ Binding to Alpha-7 nAChRs Alpha-7 nAChRs were allowed to interact with $A\beta_{1-40}$ or $A\beta_{1-42}$ and the mixture was then immunoprecipitated with anti-alpha-7 nAChR antibodies. Western analyses of the immunoprecipitated proteins identified only the presence of $A\beta_{1-42}$, indicating that the $A\beta_{1-42}$/alpha-7 nAChR interaction is robust and of high affinity. Since it has already been shown that $A\beta_{1-40}$ binds to the alpha-7 receptor, the failure in detecting $A\beta_{1-40}$ in this co-precipitation experiment suggests that the $A\beta_{1-40}$/alpha-7 nAChR interaction is of lower affinity than the $A\beta_{1-42}$/alpha-7 nAChR interaction.

EXAMPLE 14

Compound 9 inhibited $A\beta$ aggregation $A\beta$s are known to form aggregates leading to the formation of amyloid plaques that are characteristic of Alzheimer's disease. This phenomenon can be demonstrated in vitro by using Synthaloid plates, coated with $A\beta$ crystallization centers, and labelled $A\beta$s for detecting aggregation. We have validated this aggregation assay using both $^{125}I\text{-}A\beta_{1-40}$ and fluo-$A\beta_{1-40}$ in a buffer containing 50 mM HEPES, pH 7.4, 0.1% BSA, 10% FCS and protease inhibitors. About 500 pM of $^{125}I\text{-}A\beta_{1-40}$ or 100 nM of fluo-$A\beta_{1-40}$ in 100 µl of each well of the 96-well Synthaloid plate was allowed to incubate for 2.5 hr at room temperature in the presence or absence of inhibitors. At the end of the incubation, unbound protein in the wells was removed by three washes using the above buffer. The amount of bound protein which represented $A\beta$ aggregation was measured either by scintillation counting or fluorescence measurements. Compound 9 was found to potently inhibit $A\beta$ aggregation with 10 nM $IC_{50}$. Time course studies also showed that prolonged incubation of amyloid aggregates with Compound 9 resulted in disaggregation.

Compounds which inhibit $A\beta$ aggregation with an $IC_{50}$<100 micromolar may be effective in inhibiting the binding of $A\beta$ to alpha-7 in such a manner as to have a positive therapeutic effect useful for the treatment of neurodegenerative disorders.

EXAMPLE 15

Compound 9 Blocked the Effect of $A\beta$s on Acetylcholine Release from Synaptosomes Synaptosomes from guinea pig hippocampus were incubated with 0.1 µM $^3$H-choline and then subjected to repeated washes to remove unincorporated $^3$H-choline. The synaptosomes were treated with 65 mM K$^+$ for 30 seconds to elicit 3H-acetylcholine release. While $A\beta_{1-40}$ and $A\beta_{1-42}$ at 100 pM both inhibited acetylcholine release from these preparations (33% inhibition for both $A\beta_{1-40}$ and $A\beta_{1-42}$), pretreatment of the synaptosomes with both 10 nM of Compound 9 and 100 pM of either $A\beta_{1-40}$ and $A\beta_{1-42}$ prior to K$^+$ stimulation was found to have no effect on acetylcholine release.

EXAMPLE 16

Compound 9 Inhibited $^{125}I\text{-}A\beta_{1-40}$ Binding to Alpha-7 nAChRs

To determine the effect of compound 9 on $^{125}I\text{-}A\beta_{1-40}$ to alpha-7 nAChRs, alpha-7 nAChR contained SK-N-MC cell membranes were immobilized on wheat germ agglutinin coupled yittrium SPA beads and allowed to incubate with $^{125}I\text{-}A\beta_{1-40}$ in the presence of various concentrations of compound 9. The result demonstrated that Compound 9 efficiently inhibited the binding of $^{125}I\text{-}A\beta_{1-40}$ to SK-N-MC cells with a 300 pM $IC_{50}$. Compounds which inhibit the binding of $A\beta$ to alpha-7 nAChRs with an $IC_{50}$<1 micromolar may have a positive therapeutic effect useful for the treatment of neurodegenerative disorders.

EXAMPLE 17

Assay for Peptide Binding to the 206-216 Stretch of the Human α7 nAChR

A 2–5 ug quantity of the 11 amino acid peptide comprised of the 206–216 stretch of the α7 nAChR (N-Ac, C(O)NH$_2$) are added to a 96-well microtiter plate in 50 mL 10 mM HEPES, pH 7.4, or any buffer 50 ul. $^{125}I$-β-amyloid$_{1-40}$ (2000 Ci/mmol, 50 pM) was added to the wells in the presence and absence of inhibitors (1 uM to 10 uM) dissolved in 1 uL of 30% or 100% DMSO. Unbound ligands were removed and bound radioactivity was measured using a Microbeta liquid scintillation counter. Ligand binding can be inhibited by α-bugarotoxin, the peptide itself, and Compound 9.

Biological data for representative compounds of the present invention is provided in Table 2 which follows.

TABLE 2

| Cp. # | % Inh Agg. (conc µM) | % α7 nAChR 206–216 Binding | % ACh Release at 10 µM ($IC_{50}$, µM) |
|---|---|---|---|
| 9 | >90 (10) | 94 | 94 (0.1) |
| 15 | 50–90 (10) | 85 | (0.25) |
| 16 | 50–90 (10) | 44 | (10) |
| 7 | 50 (100) | NT | NT |
| 8 | 50–90 (10) | NT | (0.7) |
| 17 | >90 (10) | NT | 63 (1) |
| 18 | 50–90 (10) | NT | 70 (10) |
| 19 | 30 (5) | NT | NT |
| 20 | 39 (5) | NT | NT |
| 21 | 20 (5) | NT | NT |
| 22 | 38 (50) | NT | NT |
| 23 | NT | 54 | NT |
| 24 | NT | 43 | NT |
| 25 | NT | 48 | NT |
| 26 | <30 (10) | 64 | NT |
| 27 | NT | NT | NT |
| 28 | 50–90 (10) | 34 | NT |
| 29 | 12 (10) | NT | NT |
| 30 | 38 (5) | NT | NT |

TABLE 2-continued

| Cp. # | % Inh Agg. (conc μM) | % α7 nAChR 206–216 Binding | % ACh Release at 10 μM (IC$_{50}$, μM) |
|---|---|---|---|
| 31 | 34 (10) | NT | NT |
| 32 | 69 (10) | NT | NT |
| 33 | NT | NT | NT |
| 34 | 69 (10) | NT | NT |
| 35 | 38 (10) | NT | NT |
| 36 | <30 (10) | NT | NT |
| 37 | <30 (10) | NT | NT |
| 38 | <30 (10) | NT | NT |
| 39 | 85 (10) | NT | NT |
| 40 | 75 (10) | NT | NT |
| 41 | <30 (10) | 19 | 14 |
| 42 | 60 (10) | NT | NT |
| 43 | 50–90 (10) | 10 | 0 |
| 44 | 50–90 (10) | 23 | 0 |
| 45 | 30–50 (78) | NT | 78 |
| 46 | 50–90 (10) | 18 | 0 |
| 47 | NT | NT | NT |
| 48 | <30 (10) | 2 | 0 |
| 49 | 50–90 (10) | 0 | 17 |
| 50 | <30 (10) | 0 | 67 |
| 51 | 30–50 (10) | 0 | 54 |
| 52 | 60 (10) | 0 | 0 |
| 53 | 50–90 (10) | 0 | 18 |
| 54 | 50–90 (10) | 0 | 0 |
| 55 | 50–90 (10) | 0 | 15 |
| 56 | <30 (10) | 78 | 8 |
| 57 | <30 (10) | 63 | 11 |
| 58 | <30 (10) | 42 | 18 |
| 59 | <30 (10) | 72 | 25 |
| 60 | very active | 0 | 24 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. The method for treating Alzheimer's disease in a subject in need thereof which comprises administering to the subject an amount of a compound of the formula I

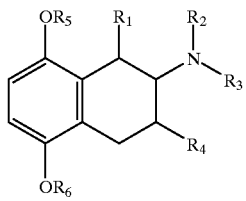

wherein $R_1$ is hydrogen or $C_1$–$C_4$ alkyl;

$R_2$ is selected from hydrogen, $C_1$–$C_6$ alkyl, aryl or $C_7$–$C_{10}$ aralkyl;

$R_3$ is selected from hydrogen, $C_1$–$C_6$ alkyl, $C_3$–$C_{10}$ alkenyl, $C_3$–$C_8$ cycloalkyl$C_1$–$C_6$ alkyl, $C_1$–$C_6$ alkoxycarbonyl$C_1$–$C_6$ alkyl, $C_1$–$C_6$ alkylthio, heteroaryl$C_1$–$C_4$ alkyl, unsubstituted or substituted aryl or unsubstituted or substituted $C_7$–$C_{10}$ aralkyl wherein the substituent on the aryl or aralkyl are one or more substituents independently selected from the group consisting of halogen, hydroxy, $C_1$–$C_6$ alkyl and unsubstituted or substituted $C_1$–$C_6$ alkoxy wherein the substituents on the alkoxy are one or more substituents independently selected from amino, $C_1$–$C_6$ alkylamino, $C_1$–$C_6$ dialkylamino, pyrrolidinyl, piperidinyl, azepinyl or morpholinyl; or $R_2$ and $R_3$, together with the nitrogen to which they are attached, form a five or six-membered heterocyclic ring selected from pyrrolidinyl, piperidinyl, morpholinyl, thiomorpholinyl or piperazinyl;

$R_4$ is $C_1$–$C_6$ alkyl, aryl, or $C_7$–$C_{10}$ aralkyl; and $R_5$ and $R_6$ are each independently selected from hydrogen, $C_1$–$C_6$ alkyl, $C_3$–$C_{10}$ alkenyl, $C_1$–$C_8$ alkylcarbonyl, or diphenylphosphinyl;

or pharmaceutically acceptable salts thereof;

effective to inhibit the binding of an amyloid beta peptide with human alpha-7 nicotinic acetylcholine receptors.

2. The method of treating dementia in an Alzheimer's disease patient which comprises administering to the patient an amount of the compound of the formula I

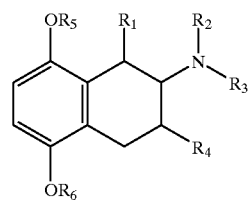

wherein $R_1$ is hydrogen or $C_1$–$C_4$ alkyl;

$R_2$ is selected from hydrogen, $C_1$–$C_6$ alkyl, aryl or $C_7$–$C_{10}$ aralkyl;

$R_3$ is selected from hydrogen, $C_1$–$C_6$ alkyl, $C_3$–$C_{10}$ alkenyl, $C_3$–$C_8$ cycloalkyl$C_1$–$C_6$ alkyl, $C_1$–$C_6$ alkoxycarbonyl$C_1$–$C_6$ alkyl, $C_1$–$C_6$ alkylthio, heteroaryl$C_1$–$C_4$ alkyl, unsubstituted or substituted aryl or unsubstituted or substituted $C_7$–$C_{10}$ aralkyl wherein the substituent on the aryl or aralkyl are one or more substituents independently selected from the group consisting of halogen, hydroxy, $C_1$–$C_6$ alkyl and unsubstituted or substituted $C_1$–$C_6$ alkoxy wherein the substituents on the alkoxy are one or more substituents independently selected from amino, $C_1$–$C_6$ alkylamino, $C_1$–$C_6$ dialkylamino, pyrrolidinyl, piperidinyl, azepinyl or morpholinyl; or $R_2$ and $R_3$, together with the nitrogen to which they are attached, form a five or six-membered heterocyclic ring selected from pyrrolidinyl, piperidinyl, morpholinyl, thiomorpholinyl or piperazinyl;

$R_4$ is $C_1$–$C_6$ alkyl, aryl, or $C_7$–$C_{10}$ aralkyl; and $R_5$ and $R_6$ are each independently selected from hydrogen, $C_1$–$C_6$ alkyl, $C_3$–$C_{10}$ alkenyl, $C_1$–$C_8$ alkylcarbonyl, or diphenylphosphinyl;

or pharmaceutically acceptable salts thereof;

effective to inhibit the binding of an amyloid beta peptide with human alpha-7 nicotinic acetylcholine receptors.

3. The method of improving memory or halting the progression of mental deterioration in an Alzheimer's disease patient which comprises administering to the patient an amount of the compound of the formula I wherein $R_1$ is hydrogen or $C_1$–$C_4$ alkyl;

$R_2$ is selected from hydrogen, $C_1$–$C_6$ alkyl, aryl or $C_7$–$C_{10}$ aralkyl;

$R_3$ is selected from hydrogen, $C_1$–$C_6$ alkyl, $C_3$–$C_{10}$ alkenyl, $C_3$–$C_8$ cycloalkyl$C_1$–$C_6$ alkyl, $C_1$–$C_6$ alkoxycarbonyl$C_1$–$C_6$ alkyl, $C_1$–$C_6$ alkylthio, heteroaryl$C_1$–$C_4$ alkyl, unsubstituted or substituted aryl or unsubstituted or substituted $C_7$–$C_{10}$ aralkyl wherein the substituent on the aryl or aralkyl are one or more substituents independently selected from the group consisting of halogen, hydroxy, $C_1$–$C_6$ alkyl and unsubstituted or substituted $C_1$–$C_6$ alkoxy wherein the substituents on the alkoxy are one or more substituents independently selected from amino, $C_1$–$C_6$ alkylamino, $C_1$–$C_6$ dialkylamino, pyrrolidinyl, piperidinyl, azepinyl or morpholinyl; or $R_2$ and $R_3$, together with the nitrogen to which they are attached, form a five or six-membered heterocyclic ring selected from pyrrolidinyl, piperidinyl, morpholinyl, thiomorpholinyl or piperazinyl;

$R_4$ is $C_1$–$C_6$ alkyl, aryl, or $C_7$–$C_{10}$ aralkyl; and $R_5$ and $R_6$ are each independently selected from hydrogen, $C_1$–$C_6$ alkyl, $C_3$–$C_{10}$ alkenyl, $C_1$–$C_8$ alkylcarbonyl, or diphenylphosphinyl;

or pharmaceutically acceptable salts thereof;

effective to inhibit the binding of an amyloid beta peptide with human alpha-7 nicotinic acetylcholine receptors.

4. The method of treating a neurodegenerative disorder in a subject in need thereof which comprises administering to the subject a therapeutically effective amount of a compound of the formula I wherein $R_1$ is hydrogen or $C_1$–$C_4$ alkyl;

$R_2$ is selected from hydrogen, $C_1$–$C_6$ alkyl, aryl or $C_7$–$C_{10}$ aralkyl;

$R_3$ is selected from hydrogen, $C_1$–$C_6$ alkyl, $C_3$–$C_{10}$ alkenyl, $C_3$–$C_8$ cycloalkyl$C_1$–$C_6$ alkyl, $C_1$–$C_6$ alkoxycarbonyl$C_1$–$C_6$ alkyl, $C_1$–$C_6$ alkylthio, heteroaryl$C_1$–$C_4$ alkyl, unsubstituted or substituted aryl or unsubstituted or substituted $C_7$–$C_{10}$ aralkyl wherein the substituent on the aryl or aralkyl are one or more substituents independently selected from the group consisting of halogen, hydroxy, $C_1$–$C_6$ alkyl and unsubstituted or substituted $C_1$–$C_6$ alkoxy wherein the substituents on the alkoxy are one or more substituents independently selected from amino, $C_1$–$C_6$ alkylamino, $C_1$–$C_6$ dialkylamino, pyrrolidinyl, piperidinyl, azepinyl or morpholinyl; or $R_2$ and $R_3$, together with the nitrogen to which they are attached, form a five or six-membered heterocyclic ring selected from pyrrolidinyl, piperidinyl, morpholinyl, thiomorpholinyl or piperazinyl;

$R_4$ is $C_1$–$C_6$ alkyl, aryl, or $C_7$–$C_{10}$ aralkyl; and $R_5$ and $R_6$ are each independently selected from hydrogen, $C_1$–$C_6$ alkyl, $C_3$–$C_{10}$ alkenyl, $C_1$–$C_8$ alkylcarbonyl, or diphenylphosphinyl;

or pharmaceutically acceptable salts thereof.

5. The method of treating a neurodegenerative disorder as in claim 4, wherein the compound of formula I, $R_1$ is hydrogen;

$R_2$ is selected from hydrogen or $C_1$–$C_4$ alkyl;

$R_3$ is selected from $C_1$–$C_4$ alkyl, $C_3$–$C_{10}$ alkenyl, $C_5$–$C_6$ cycloalkyl$C_1$–$C4_6$ alkyl, $C_1$–$C_6$ alkoxycarbonyl$C_1$–$C_4$ alkyl, $C_1$–$C_6$ alkylthio, heteroaryl$C_1$–$C_4$ alkyl, or unsubstituted or substituted $C_7$–$C_{10}$ aralkyl wherein the substituent on the aralkyl are one or two substituents independently selected from the group consisting of halogen, hydroxy, $C_1$–$C_4$ alkyl and unsubstituted or substituted $C_1$–$C_4$ alkoxy wherein the substituents on the alkoxy are one or two substituents independently selected from amino, $C_1$–$C_4$ alkylamino, $C_1$–$C_4$ dialkylamino, pyrrolidinyl, or piperidinyl; or $R_2$ and $R_3$, together with the nitrogen to which they are attached, form a morpholinyl ring;

$R_4$ is $C_1$–$C_4$ alkyl; and $R_5$ and $R_6$ are each independently selected from hydrogen, $C_1$–$C_4$ alkyl, $C_3$–$C_6$ alkenyl, $C_1$–$C_6$ alkylcarbonyl, or diphenylphosphinyl;

or pharmaceutically acceptable salts thereof.

6. The method of treating a neurodegenerative disorder as in claim 4, wherein the compound of formula I is a compound of the formula I wherein $R_1$ is hydrogen or $C_1$–$C_4$ alkyl;

$R_2$ and $R_3$ are each independently selected from hydrogen, $C_1$–$C_6$ alkyl, aryl or $C_7$–$C_{10}$ aralkyl; and $R_4$ is $C_1$–$C_6$ alkyl, aryl, or $C_7$–$C_{10}$ aralkyl, or pharmaceutically acceptable salts thereof.

7. A method of treating a neurodegenerative disorder as in claim 6, wherein the compound is 5,8-dihydroxy-trans-2-di(N-propylamino)-3-methyl-1,2,3,4-tetrahydronaphthalene or pharmaceutically acceptable salts thereof.

8. The method of claim 4, wherein the neurodegenerative disorder is selected from group consisting of Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infaction intracranial and intravertebral lesions, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, or Finnish and Iowa amyloidosis.

9. The method of claim 4, wherein the neurodegenerative disorder is Alzheimer's disease.

10. The method of claim 4, wherein the neurodegenerative disorder is dementia in an Alzheimer's disease patient.

11. The method of claim 4, wherein the neurodegenerative disorder is diminished memory or mental deterioration in an Alzheimer's disease patient.

12. The method of claim 1, wherein the amyloid beta peptide is $A\beta_{1-42}$.

13. The method of claim 2, wherein the amyloid beta peptide is $A\beta_{1-42}$.

14. The method of claim 3, wherein the amyloid beta peptide is $A\beta_{1-42}$.

* * * * *